(12) United States Patent
Kim et al.

(10) Patent No.: US 7,884,623 B2
(45) Date of Patent: Feb. 8, 2011

(54) DETECTOR

(75) Inventors: Seong Hyun Kim, Daejeon (KR); Yong Suk Yang, Daejeon (KR); Sang Chul Lim, Daejeon (KR); Zin Sig Kim, Daejeon (KR); Yoon Ho Song, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 371 days.

(21) Appl. No.: 12/181,819

(22) Filed: Jul. 29, 2008

(65) Prior Publication Data

US 2009/0146639 A1 Jun. 11, 2009

(30) Foreign Application Priority Data

Dec. 5, 2007 (KR) .................. 10-2007-0125549

(51) Int. Cl.
*G01R 27/26* (2006.01)
*G01R 27/08* (2006.01)

(52) U.S. Cl. .................................... 324/663; 324/713

(58) Field of Classification Search ................ 324/713, 324/691, 649, 600, 158.1, 76.11, 663, 660, 324/658, 664, 686, 689, 717; 438/17, 14, 438/455
See application file for complete search history.

(56) References Cited

U.S. PATENT DOCUMENTS

| | | | |
|---|---|---|---|
| 6,331,476 B1 | 12/2001 | Kawakita et al. | |
| 7,061,010 B2 * | 6/2006 | Minakata | 257/40 |
| 7,265,003 B2 | 9/2007 | Hoffman et al. | |
| 2003/0085719 A1 * | 5/2003 | Yoon et al. | 324/663 |
| 2006/0169045 A1 | 8/2006 | Shinohara et al. | |
| 2007/0269344 A1 * | 11/2007 | Ohnishi et al. | 422/68.1 |

FOREIGN PATENT DOCUMENTS

| | | |
|---|---|---|
| KR | 10-2004-0029402 | 4/2004 |
| KR | 10-2007-0039335 | 4/2007 |

OTHER PUBLICATIONS

Ko et al., Electrochemical Detection of Cardiac Troponin I Using a Microchip with the Surface-Functionalized Poly(dimethylsiloxane) Channel, Biosensors and Bioelectronics, vol. 23, Mar. 30, 2007, p. 51-59.

* cited by examiner

*Primary Examiner*—Hoai-An D Nguyen
(74) *Attorney, Agent, or Firm*—Rabin & Berdo, PC

(57) ABSTRACT

Provided is a detector having a transistor or resistor structure. When an electrode is exposed to a detected solution, such as blood, a variation in current flowing through the detected solution may be greater than a variation in the electrical characteristics of the detector caused by a variation in the physical properties of semiconductor so that it is difficult to detect whether a bio-particle is contained in the detected solution. In order to solve this problem, a detection portion and an electrical measurement portion are separately formed, and the detection portion is processed with the bio-particle and then post-processed. Subsequently, the detection portion and the electrical measurement portion are bonded to each other using, for example, a laminating process, and the detector measures a detection value.

7 Claims, 1 Drawing Sheet

DETECTOR

CROSS-REFERENCE TO RELATED APPLICATION

This application claims priority to and the benefit of Korean Patent Application No. 2007-125549, filed Dec. 5, 2007, the disclosure of which is incorporated herein by reference in its entirety.

BACKGROUND

1. Field of the Invention

The present invention relates to a detector for detecting a specific functional group in a fluid and, more particularly, to a detector, which is a bio-device formed of an organic semiconductor, is fabricated by a semiconductor fabrication process, and detects a specific chemical functional group in a fluid.

2. Discussion of Related Art

Conventionally, a detector is formed using an inorganic semiconductor so that an electrode is protected using an organic material, such as polydimethylsiloxane (PDMS), and a bio-solution is flowed on a semiconductor portion to measure characteristics of the semiconductor portion.

In this case, however, the fabrication of the detector is costly so that the detector is not appropriate for a disposable or portable detector. Accordingly, it is necessary to develop an ultra-low-cost detector that may be fabricated using a printing technique, such as an inkjet printing technique, and measure the characteristics of a semiconductor in a simple manner.

Accordingly, a semiconductor detector using an organic semiconductor as ink has been proposed so as to reduce fabrication cost. However, in order to detect a specific protein or carbohydrate, a bio-solution, such as blood, must be coated on the semiconductor detector and the electrical characteristics of the semiconductor detector must be measured. However, a variation in current flowing through the bio-solution may be greater than a variation in the electrical characteristics of the semiconductor detector caused by a variation in the characteristics of the semiconductor detector. In this case, the characteristics of the semiconductor detector may not be precisely measured.

In order to solve the above-described problems, an electrode may be protected by a polymer, such as polydimethylsiloxane (PDMS), and a bio-solution may be brought into contact with only a channel region. In this case, however, the fabrication process of a detector is complicated, thereby increasing fabrication cost. Furthermore, an area of contact of a semiconductor with a bio-solution (e.g., blood) is reduced, thereby degrading the detection performance of the detector.

SUMMARY OF THE INVENTION

The present invention is directed to a detector that may be fabricated at a low cost using a semiconductor fabrication process.

Also, the present invention is directed to a detector that is superior in detection performance to conventional detectors.

Furthermore, the present invention is directed to a detector that is more capable of detecting a specific component, such as a protein or a carbohydrate contained in a bio-solution, than conventional detectors and may be fabricated at a low cost.

When a detector having a transistor or resistor structure is fabricated, a variation in current flowing through the detected solution may be greater than a variation in the electrical characteristics of the detector caused by a variation in the physical properties of a semiconductor so that it would be difficult to detect whether a bio-particle is contained in the detected solution. In order to overcome this drawback, according to the present invention, a detection portion and an electrical measurement portion are separately formed. Thereafter, the detection portion is processed with the bio-particle and post-processed. Subsequently, the detection portion and the electrical measurement portion are bonded to each other using, for example, a laminating process, and the detector may measure a detection value.

One aspect of the present invention provides a detector including a first substrate and a second substrate. The first substrate includes a first electrode, a dielectric layer enclosing top and lateral surfaces of the first electrode, and second and third electrodes disposed apart from each other on a portion of a top surface of the dielectric layer. The second substrate includes a second frame substrate and a reactant layer which is disposed on the frame substrate and reacts with a specific functional group.

When the reactant layer contacts a fluid to be measured, the first substrate is closely bonded to the second substrate so that the detector can measure electrical characteristics between the second and third electrodes.

Another aspect of the present invention provides a detector including a first substrate and a second substrate. The first substrate includes a first frame substrate and first and second electrodes disposed apart from each other on a portion of a top surface of the first frame substrate. The second substrate includes a second frame substrate and a reactant layer which is disposed on the second frame substrate and reacts with a specific functional group.

When the reactant layer contacts a fluid to be measured, the first substrate is closely bonded to the second substrate so that the detector can measure electrical characteristics between the first and second electrodes.

BRIEF DESCRIPTION OF THE DRAWINGS

The above and other features and advantages of the present invention will become more apparent to those of ordinary skill in the art by describing in detail exemplary embodiments thereof with reference to the attached drawings in which.

DETAILED DESCRIPTION OF EMBODIMENTS

In the present invention, a detector for detecting a specific functional group that may be produced in large quantities using a semiconductor fabrication process is proposed. In order to improve detection performance and reduce fabrication cost, a first substrate for measuring electrical characteristics and a second substrate for contacting a fluid to be detected are separately fabricated. Thereafter, during a detection process, the fluid is brought into contact with the second substrate, and the first and second substrates are closely bonded to each other, thereby obtaining a result of detection of a functional group.

The use of the detector will now be described in detail. The surface of a reactant layer included in the second substrate is processed with a bio-solution so that a semiconductor can sufficiently combine with a protein or a carbohydrate contained in the bio-solution. Thereafter, the surface of the reactant layer is cleaned using distilled water or dried. Subsequently, the first and second substrates are bonded to each other using a lamination process, and the electrical characteristics of an electrical characteristic unit are measured.

The above-described method may not involve installing an electrode protection structure, thereby reducing the number of process steps. Also, since the processed surface of the reactant layer corresponds to a channel of a transistor, a variation in the characteristics of the transistor is increased so that a highly precise detector can be fabricated.

The present invention will be described more fully hereinafter with reference to the accompanying drawings, in which exemplary embodiments of the invention are shown. This invention may, however, be embodied in different forms and should not be construed as limited to the embodiments set forth herein.

Embodiment 1

Figure 1:
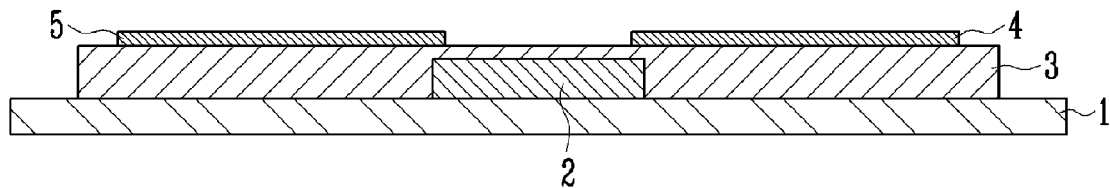
FIG. 1 is a cross-sectional view of a first substrate of a detector according to an exemplary embodiment of the present invention.

FIG. 1 is a cross-sectional view of a first substrate of a detector according to an exemplary embodiment of the present invention. The first substrate shown in FIG. 1 is an electrical characteristic measurement portion having a transistor structure.

Referring to FIG. 1, a first electrode 2 corresponding to a gate electrode is disposed on a first frame substrate 1, and a dielectric layer 3 is disposed on the first electrode 2. Second and third electrodes 4 and 5 corresponding to source and drain electrodes are disposed on the dielectric layer 3. Thus, the first electrode 2, the second electrode 4, and the third electrode 5 form a transistor having about the same structure as a metal-oxide-semiconductor (MOS) transistor. The first substrate is used to measure electrical characteristics (e.g., voltage and/or current) between the source and drain electrodes (i.e., the first and second electrodes) so as to check whether the electrical characteristics are detected or estimate a detected amount.

The first frame substrate 1 may be a silicon wafer, a glass substrate, or a plastic substrate. The plastic substrate may be a polyethylene terephtalate (PET) substrate, a polyethersulfone (PES) substrate, a polyethylene naphthalate (PEN) substrate, or a polyimide (PI) substrate.

Each of the first electrode 2, the second electrode 4, and the third electrode 5 may be formed of a conductive material to function as an electrode. Specifically, each of the first through third electrodes 2, 4, and 5 may be formed of at least one of organic and inorganic conductive materials.

For example, each of the first through third electrodes 2, 4, and 5 may be formed of a metal, a metal compound, or a doped or undoped conductive polymer. The metal may be gold (Au), silver (Ag), aluminum (Al), chrome (Cr), or titanium (Ti). The metal compound may be tungsten silicide or titanium nitride. The conductive polymer may be PANi, polyacethlene, polyaniline, polyisothianaphthene, or PEDOT.

Figure 2:
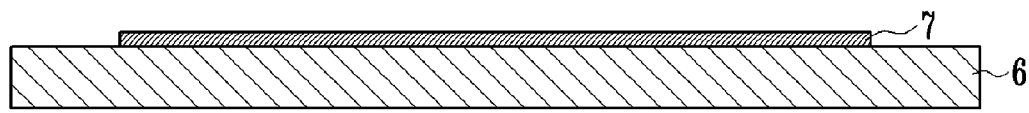
FIG. 2 is a cross-sectional view of a second substrate of a detector according to an exemplary embodiment of the present invention.

FIG. 2 is a cross-sectional view of a second substrate of a detector according to an exemplary embodiment of the present invention. The second substrate shown in FIG. 2 is a detection reactor having an organic semiconductor layer.

Referring to FIG. 2, a reactant layer 7 is disposed on a second frame substrate 6. The reactant layer 7 may be formed of an organic semiconductor. However, the present invention is not limited thereto and the reactant layer 7 may be formed of at least one selected from the group consisting of a semiconductor polymer, a conductive polymer, derivatives thereof, and derivatives of the organic semiconductor.

The second frame substrate 6 may also be a silicon wafer, a glass substrate, or a plastic substrate. The plastic substrate may be a PET substrate, a PES substrate, a PEN substrate, or a PI substrate.

Meanwhile, in order to increase adhesion of the first substrate with the second substrate, at least one of the first frame substrate 1 of the first substrate and the second frame substrate 6 of the second substrate may be formed of a polydimethylsiloxane (PDMS) material cross-linked by a cross-linking agent. This is because adhesion between PDMS materials, adhesion between PDMS and silicon, and adhesion between PDMS and glass are reliable. Accordingly, when only one of the first and second frame substrates 1 and 6 is formed of a cross-linked PDMS material, the other one may be formed of silicon or glass.

The organic semiconductor may contain a component that is bonded to a bio-molecule to be detected, such as a specific protein or carbohydrate. For example, the organic semiconductor may be poly-3-hexylthiophene (P3HT) or poly(9,9-dioctylfluorene-co-bithiophene) (F8T2), and when biotin is bonded to a side chain of P3HT or F8T2, the biotin is strongly bonded to avidin protein contained in a target solution. In other words, the avidin protein becomes a functional group to be detected.

The organic semiconductor has semiconductor characteristics before the organic semiconductor is bonded to the functional group, while the organic semiconductor exhibits about the same characteristics as an insulator after the organic semiconductor is bonded to the functional group (however, the organic semiconductor is still referred to as the organic semiconductor because it has the semiconductor characteristics in a normal state). Therefore, it may be detected whether a specific protein is contained in a bio-solution depending on a variation in the characteristics of the organic semiconductor.

The fabrication of the detector according to the present embodiment is completed in a state that the first substrate of FIG. 1 and the second substrate of FIG. 2 remain separated from each other. A process of detecting a bio-solution, such as blood, using the above-described detector will now be described.

At the outset, a bio-solution to be detected is brought into contact with the reactant layer 7 of the second substrate. Specifically, the bio-solution, which is diluted at a concentration for facilitating the detection process, may be dripped on the reactant layer 7, or the second substrate including the reactant layer 7 may be dipped in the bio-solution. A time taken for the reactant layer 7 to contact the bio-solution may be variously selected according to the type of a material to be detected or detection conditions.

Thereafter, the bio-solution remaining on the second substrate is removed or dried.

Subsequently, the first substrate is bonded to the second substrate. Specifically, the first and second substrates may be closely adhered to each other by a guide or contact frame for applying physical pressure to the first and second substrates. Alternatively, the first and second substrates may be bonded to each other using a semiconductor bonding process, such as a laminating process. As can be seen from FIG. 3, the first substrate is bonded to the second substrate such that a portion of a top surface of the dielectric layer 3 interposed between the first and second electrodes 4 and 5 of the first substrate comes into close contact with the reactant layer 7 of the second substrate.

Thereafter, electrical characteristics (e.g., voltage, current, and resistance) between the second and third electrodes 4 and 5 of the first substrate are measured.

Figure 3:
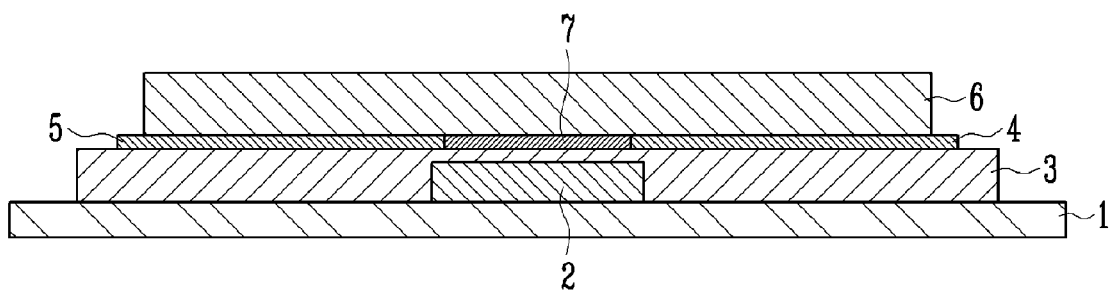
FIG. 3 is a cross-sectional view of a bonded structure of the first substrate of FIG. 1 and the second substrate of FIG. 2.

FIG. 3 shows a bonded structure of the first and second substrates. In the bonded structure, since the portion of the top surface of the reactant layer 7 that is bonded to a specific protein becomes a channel of a transistor, a variation in the characteristics of the transistor is marked. For instance, a difference between resistances measured before and after the reactant layer 7 is bonded to a bio-molecule (e.g., a protein) to be detected may be measured, so that it can be checked whether the protein is contained or the amount of protein may be estimated based on the measured variation in resistance.

Embodiment 2

Figure 4:
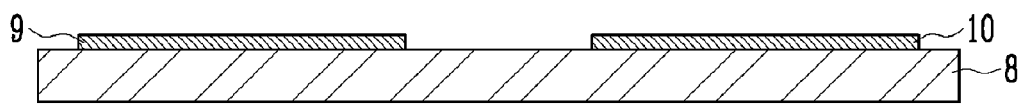
FIG. 4 is a cross-sectional view of a first substrate of a detector according to another exemplary embodiment of the present invention.

FIG. 4 is a cross-sectional view of a first substrate of a detector according to another exemplary embodiment of the present invention. The first substrate shown in FIG. 4 is an electrical characteristic measurement portion having a transistor structure.

Referring to FIG. 4, unlike in the embodiment shown in FIG. 1, a first electrode 9 and a second electrode 10 are disposed directly on a first frame substrate 8 without preparing a gate electrode. In other words, the first and second electrodes 9 and 10 are used to obtain an electrical signal for checking whether a material to be detected is contained or estimating a detected amount as in the previous embodiment. However, the first substrate cannot form a MOS transistor structure so that the first and second electrodes 9 and 10 are not referred to as source and drain electrodes.

The first frame substrate 8 may be a silicon wafer, a glass substrate, or a plastic substrate. The plastic substrate may be a PET substrate, a PES substrate, a PEN substrate, or a PI substrate. Alternatively, the first frame substrate 8 of the first substrate may be formed of a PDMS material in order to increase adhesion of the first substrate with a second substrate.

Each of the first and second electrodes 9 and 10 may be formed of a conductive material to function as an electrode. Specifically, each of the first and second electrodes 9 and 10 may be formed of at least one of organic and inorganic conductive materials.

For example, each of the first and second electrodes 9 and 10 may be formed of a metal, a metal compound, or a doped or undoped conductive polymer. The metal may be gold (Au), silver (Ag), aluminum (Al), chrome (Cr), or titanium (Ti). The metal compound may be tungsten silicide or titanium nitride. The conductive polymer may be PANi, polyacethlene, polyaniline, polyisothianaphthene, or PEDOT.

In the present embodiment, the second substrate, which functions as detection reactor, may be the same as in the previous embodiment. Thus, a detailed description of the second substrate will be omitted here.

As in the previous embodiment, the fabrication of the detector is completed when the first and second substrates remain separated from each other. The first and second substrates are bonded to each other during a detection process.

Figure 5:
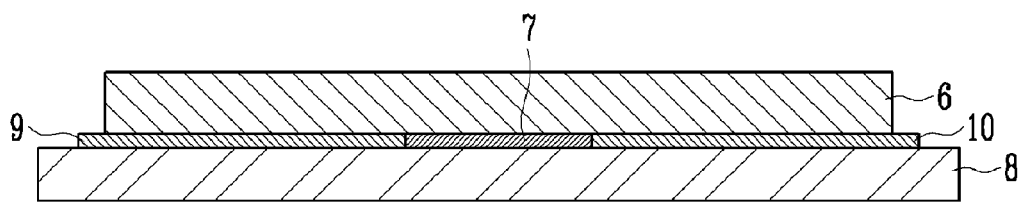
FIG. 5 is a cross-sectional view of a bonded structure of the first substrate of FIG. 4 and the second substrate of FIG. 2.

FIG. 5 is a cross-sectional view of a bonded structure of the first substrate of FIG. 4 and the second substrate of FIG. 2. As in the previous embodiment, since a portion that is bonded to a molecule of a component (e.g., a specific protein) to be detected becomes a channel of a transistor, a variation in the characteristics of the transistor is marked. Although, unlike in the previous embodiment, an additional structure corresponding to a gate electrode is not disposed, a variation in the characteristics of a reactant layer may be sufficiently measured using the first and second electrodes 8 and 6. Meanwhile, in the present embodiment, the formation of the third electrode is omitted, thereby reducing the fabrication cost of the detector.

According to the present invention as described above, a structure for protecting an electrode is not formed so that the fabrication cost of a detector can be reduced.

Also, the detector according to the present invention can detect a specific functional group easily and precisely using an electronic device having a transistor structure.

In the drawings and specification, there have been disclosed typical preferred embodiments of the invention and, although specific terms are employed, they are used in a generic and descriptive sense only and not for purposes of limitation. As for the scope of the invention, it is to be set forth in the following claims. Therefore, it will be understood by those of ordinary skill in the art that various changes in form and details may be made therein without departing from the spirit and scope of the present invention as defined by the following claims.

What is claimed is:

1. A detector comprising:
    a first substrate including a first electrode, a dielectric layer enclosing top and lateral surfaces of the first electrode, and second and third electrodes disposed apart from each other on a portion of a top surface of the dielectric layer; and
    a second substrate including a frame substrate, and a reactant layer which is disposed on the frame substrate and reacts with a specific functional group,
    wherein when the reactant layer contacts a fluid to be measured, the first substrate is closely bonded to the second substrate so that the detector measures electrical characteristics between the second and third electrodes.

2. The detector according to claim 1, wherein the second and third electrodes are not disposed on a portion of the top surface of the dielectric layer that overlaps the first electrode.

3. The detector according to claim 1, wherein the first electrode is a gate electrode, the second electrode is a source electrode, the third electrode is a drain electrode, and the first, second, and third electrodes form a transistor.

4. The detector according to claim 1, wherein the reactant layer is formed of at least one material selected from the group consisting of an organic semiconductor, a semiconductor polymer, a conductive polymer, and derivatives thereof.

5. The detector according to claim 1, wherein the first substrate further comprises a frame substrate disposed under the first electrode to support the first electrode.

6. A detector comprising:
    a first substrate including a first frame substrate and first and second electrodes disposed apart from each other on a portion of a top surface of the first frame substrate; and
    a second substrate including a second frame substrate, and a reactant layer which is disposed on the second frame substrate and reacts with a specific functional group,
    wherein when the reactant layer contacts a fluid to be measured, the first substrate is closely bonded to the second substrate so that the detector measures electrical characteristics between the first and second electrodes.

7. The detector according to claim 6, wherein the reactant layer is formed of at least one material selected from the group consisting of an organic semiconductor, a semiconductor polymer, a conductive polymer, and derivatives thereof.

* * * * *